(12) United States Patent
Makino et al.

(10) Patent No.: US 10,330,692 B2
(45) Date of Patent: Jun. 25, 2019

(54) AUTOMATIC ANALYSIS DEVICE

(71) Applicant: HITACHI HIGH-TECHNOLOGIES CORPORAITON, Tokyo (JP)

(72) Inventors: Akihisa Makino, Tokyo (JP); Chie Yabutani, Tokyo (JP); Masato Ishizawa, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 80 days.

(21) Appl. No.: 15/035,275

(22) PCT Filed: Nov. 5, 2014

(86) PCT No.: PCT/JP2014/079280
§ 371 (c)(1),
(2) Date: May 9, 2016

(87) PCT Pub. No.: WO2015/093166
PCT Pub. Date: Jun. 25, 2015

(65) Prior Publication Data
US 2016/0291048 A1 Oct. 6, 2016

(30) Foreign Application Priority Data
Dec. 20, 2013 (JP) ................................ 2013-263204

(51) Int. Cl.
*G01N 35/02* (2006.01)
*G01N 35/04* (2006.01)
(52) U.S. Cl.
CPC ........... *G01N 35/026* (2013.01); *G01N 35/04* (2013.01); *G01N 2035/0462* (2013.01); *G01N 2035/0467* (2013.01); *G01N 2035/0472* (2013.01)
(58) Field of Classification Search
None
See application file for complete search history.

(56) References Cited

U.S. PATENT DOCUMENTS 4,451,433 A 5/1984 Yamashita et al.
5,972,295 A * 10/1999 Hanawa ........... G01N 35/00603
422/63
(Continued)

FOREIGN PATENT DOCUMENTS

JP 2000-321286 A 11/2000
JP 2001-004636 A 1/2001
(Continued)

OTHER PUBLICATIONS

International Search Report of PCT/JP2014/079280 dated Feb. 17, 2015 and International Preliminary Examination Report dated Jul. 17, 2015.
(Continued)

*Primary Examiner* — Benjamin R Whatley
(74) *Attorney, Agent, or Firm* — Mattingly & Malur, PC

(57) ABSTRACT

The purpose of the present invention is to provide an automatic analysis device that combines a biochemical analysis unit and a blood coagulation analysis unit and has a high processing capacity while reducing device cost and life-cycle cost. An automatic analysis device is characterized in that when a synthetic-substrate item or latex-agglutination item from among synthetic-substrate, latex-agglutination, and clotting-time blood-coagulation-test items is made to be a first test item and the clotting-time item is made to be a second test item, if there is a measurement request for the first test item and second test item in the same specimen rack, a control unit determines the conveyance path of the specimen rack such that the first test item is measured using a biochemical analysis unit and the second test item is measured using a coagulation time analysis unit and controls a conveyance line.

13 Claims, 12 Drawing Sheets

(56) References Cited

U.S. PATENT DOCUMENTS

| | | | | |
|---|---|---|---|---|
| 2003/0235514 A1* | 12/2003 | Nogawa | ............... | G01N 35/026 422/65 |
| 2008/0044912 A1* | 2/2008 | Yamamoto | ........... | G01N 21/272 436/69 |
| 2008/0310999 A1 | 12/2008 | Yagi et al. | | |
| 2008/0318323 A1* | 12/2008 | Shintani | ................ | B01L 3/5082 436/47 |
| 2010/0066996 A1* | 3/2010 | Kosaka | ................. | G01F 23/292 356/39 |
| 2015/0104351 A1* | 4/2015 | Makino | .................. | G01N 21/82 422/64 |

FOREIGN PATENT DOCUMENTS

| | | | | |
|---|---|---|---|---|
| JP | 2001-027639 | A | | 1/2001 |
| JP | 2001013151 | A | * | 1/2001 |
| JP | 2001-208760 | A | | 8/2001 |
| JP | 2003-057251 | A | | 2/2003 |
| JP | 2003057251 | A | * | 2/2003 |
| JP | 2008-039554 | A | | 2/2008 |
| JP | 4576393 | B2 | * | 11/2010 |
| JP | 4576393 | B2 | | 11/2010 |
| JP | 2011-013151 | A | | 1/2011 |
| WO | 2006/107016 | A1 | | 10/2006 |
| WO | 2013/187210 | A1 | | 12/2013 |

OTHER PUBLICATIONS

Japanese Office Action received in corresponding Japanese Application No. 2015-553417 dated Jul. 24, 2018.

* cited by examiner

AUTOMATIC ANALYSIS DEVICE

TECHNICAL FIELD

The present invention relates to an automatic analysis device which analyzes a component amount contained in a sample (hereinafter, also referred to as a specimen) such as blood and urine, and particularly relates to an automatic analysis device which can measure a biochemical test item and a blood coagulation test item.

BACKGROUND ART

As an analysis device which analyzes a component amount contained in a sample, an automatic analysis device is known which measures the intensity of transmitted light or scattered light having a single or multiple wavelengths obtained by emitting light from a light source to a reaction solution in which the sample and a reagent are mixed with each other, and which calculates the component amount, based on a relationship between light intensity and density.

According to an automatic analysis device disclosed in PTL 1, optically transparent reaction cells are circumferentially arrayed on a reaction disk which repeatedly rotates and stops. While the reaction disk rotates, a time-dependent change (reaction process data) of the light intensity which is caused by a reaction is measured at regular time intervals, for approximately 10 minutes, by a transmitted light measurement unit arranged in advance. After the reaction is completed, a reaction vessel is cleaned by a cleaning mechanism, and is reused for another analysis.

In a case of the reaction of the reaction solution, two analysis fields such as colorimetric analysis using a color reaction of a substrate and an enzyme and homogeneous immunological analysis using an agglutination reaction caused by binding of an antigen and an antibody are present in a broad sense. In the latter homogeneous immunological analysis, a measurement method is known such as immune-nephelometry and a latex agglutination method.

According to the immune-nephelometry, a reagent containing the antibody is used, an immune complex with a measurement object (antigen) contained in a sample is generated, and both of these are optically detected so as to quantify a component amount thereof. According to the latex agglutination method, a reagent containing latex particles in which the antibody is sensitized on (bound with) the surface is used, latex particles are coagulated through an antigen-antibody reaction with the antigen contained in a sample, and both of these are optically detected so as to quantify a component amount thereof.

In addition, an automatic analysis device disclosed in PTL 2 is also present which measures the coagulation ability of the blood. The blood flows in the blood vessel while holding liquidity. However, if the blood flows out once from a body, coagulation factors present in plasma and platelets are serially activated, and fibrinogen in the plasma is converted into fibrin and precipitated, thereby leading to hemostasis.

This coagulation ability of the blood includes exogenous ability by which the blood leaking out from the blood vessel coagulates and endogenous ability by which the blood in the blood vessel coagulates. Measurement items relating to the coagulation ability of the blood (blood clotting-time) include prothrombin time (PT) of an extrinsic blood coagulation reaction test, activated partial thromboplastin time (APTT) of an intrinsic blood coagulation reaction test, and a fibrinogen amount (Fbg).

Any of these items is configured so that fibrin precipitated by adding a reagent for initiating a coagulation reaction is detected by using optical, physical, and electrical methods. As a method of using optical means, a method is known in which a clotting-time is calculated by emitting light to a reaction solution and detecting a time-dependent intensity change in scattered light or transmitted light from the fibrin precipitated in the reaction solution. According to a representative automatic analysis device of blood coagulation in PTL 2, a blood clotting-time item requires photometric data at intervals of 0.1 seconds. Thus, the reaction is performed in a separate photometric port. If the reaction solution coagulates, a reaction vessel cannot be reused by cleaning. Thus, the reaction vessel has to be discarded. In addition to blood clotting-time measurement, a blood coagulation/fibrinolysis test field also includes coagulation factor measurement and coagulation/fibrinolysis marker measurement. Although the coagulation factor is mainly analyzed by the blood clotting-time measurement, a coagulation/fibrinolysis marker is analyzed by a synthetic substrate method using a chromogenic synthetic substrate or by the previously described latex agglutination method. The blood clotting-time item substantially and stereotypically includes PT, APTT, and Fbg in the related art. In contrast, in addition to D-dimer or fibrin/fibrinogen degradation products (FDP), a coagulation/fibrinolysis marker item includes a soluble fibrin monomer complex (SFMC) and a plasmin-α2 plasmin inhibitor (PIC). The coagulation/fibrinolysis marker item is expected to increase in the future, since there is a demand for early diagnosis/treatment of disseminated intravascular coagulation (DIC). Accordingly, it is desirable to improve a throughput of the automatic analysis device. The blood clotting-time measurement is usually completed within approximately 3 minutes. Therefore, it is possible to maintain the improved throughput by discarding/supplying a reaction vessel after the measurement is completed. On the other hand, according to the synthetic substrate method or the latex agglutination method, the reaction usually continues for 10 minutes. In most cases, the measurement time is longer than that for an item of the clotting-time method. However, according to the automatic analysis device of the blood coagulation in PTL 2, not only the clotting-time but also the coagulation/fibrinolysis marker is analyzed by using a fixed photometric port. Consequently, if there is a measurement request for a synthetic substrate item or a latex agglutination item, there is a problem in that the throughput of the device is extremely decreased. It is conceivable to employ a method of increasing the number of measurement ports in order to suppress the decrease in the throughput of the blood coagulation analysis device. However, the device cost inevitably increases, since the number of light sources, light receiving elements, and amplifier circuits which are required for detection also increases.

CITATION LIST

Patent Literature

PTL 1: U.S. Pat. No. 4,451,433
PTL 2: JP-A-2000-321286
PTL 3: Japanese Patent No. 4576393

SUMMARY OF INVENTION

Technical Problem

An automatic analysis device for clinical examination is known such as a stand-alone-type which is operated as a respectively independent device, and a module-type (refer to PTL 3) which is operated as a single device in which analysis units in multiple analysis fields such as biochemistry and immunity are connected to each other by a specimen rack conveyance line in order to streamline operations in a laboratory. The automatic analysis device of the module-type has multiple analysis units which analyze a reaction solution obtained through a reaction after mixing a sample and a reagent with each other. As a method of supplying the sample to the analysis units, a method is known in which a specimen rack accommodating a sample container is positioned at a sample suction position in the analysis units via a conveyance line.

A biochemical analysis unit and a blood coagulation analysis unit are integrally modularized. In this manner, advantageous effects can be expected in that specimen management flow is improved and device management is simplified. However, if the biochemical analysis unit and the blood coagulation analysis unit are simply integrated with each other, measurement of the blood coagulation test items cannot be performed so as to improve the throughput. Moreover, there is a possibility that the throughput of the overall device including the biochemical analysis unit may decrease. The reason is that in a case of the synthetic substrate item/latex agglutination item of the blood coagulation test items, a reaction time is predetermined for every item similarly to the biochemical test item (for example, 10 minutes). Accordingly, scheduling is facilitated, and samples are continuously dispensed one after another to the analysis unit, thereby enabling the improved throughput to be maintained. However, in a case of the clotting-time measurement item, the reaction time varies depending on the samples (for example, 3 minutes to 7 minutes), and the clotting-time measurement item needs to be measured by using a fixed measurement port. Consequently, if the measurement port installed at multiple locations is occupied, the next sample cannot be dispensed until the measurement port is vacant, and the specimen rack becomes jammed on the conveyance line. In order to solve this problem, it is conceivable to employ a method of increasing the number of the measurement ports or a method in which the inside of the analysis unit is stocked with the samples collected from the specimen rack during a certain period of time. However, any method inevitably leads to a significant increase in the device cost.

In addition, at a jobsite for clinical examination, in order to shorten a patient's waiting time for a medical examination, an effort to quickly report a result within 30 minutes from blood collection is actively made. With regard to a retest of the blood coagulation test items, determination on whether or not the clotting-time item needs to be retested is performed earlier compared to that in a case of the synthetic substrate item/latex agglutination item. Nevertheless, if the retest starts after waiting for the determination on whether or not all the requested test items in a specimen need to be retested as in the related art, a shortened turnaround time or an improved throughput cannot be further expected, compared to that under current circumstances.

Solution to Problem

Representative features according to the present invention are as follows. There is provided an automatic analysis device including a conveyance line that conveys a specimen rack accommodating a specimen container (also referred to as a sample container) which holds a specimen, a first dispensing line that is arranged along the conveyance line, and that can cause the specimen rack disposed at multiple locations to stand by the specimen which awaits dispensing, a biochemical analysis unit that aspirates the specimen on the first dispensing line, and that analyzes a biochemical analysis item in which a reaction time of a reagent and the specimen is predetermined, a second dispensing line that is arranged along the conveyance line, and that can cause the specimen rack disposed at multiple locations to stand by the specimen which awaits dispensing, a clotting-time analysis unit that aspirates the specimen on the second dispensing line, and that analyzes a clotting-time item in which the reaction time of the reagent and the specimen varies depending on the specimen, a reading unit that reads analysis request information for the specimen, and a control unit that determines a conveyance path of the specimen rack, based on the information of the reading unit, and that controls the conveyance line. When a synthetic substrate item or a latex agglutination item is set to be a first test item and a clotting-time item is set to be a second test item from among the synthetic substrate item, the latex agglutination item, and the clotting-time item in blood coagulation test items, in a case where there is a measurement request for the first test item and the second test item in the same specimen rack, the control unit determines the conveyance path of the specimen rack so that the biochemical analysis unit measures the first test item and the clotting-time analysis unit measures the second test item, and controls the conveyance line.

Furthermore, a sample dispensing line of the clotting-time analysis unit is provided with a function which can perform sampling by having access to the specimen container on the specimen rack while the racks are arranged back and forth in random order. When a retest is performed, it is not necessary to await determination on whether or not all request items for the specimen mounted on the specimen rack need the retest. The retest can be performed in random order from the clotting-time item in which the determination on whether or not the retest is needed is earlier compared to the synthetic substrate item/latex agglutination item. Therefore, a shortened turnaround time or an improved throughput can be expected.

Any method of conveying the specimen rack is applicable as long as the method can move the rack, such as a belt conveyor system and a pushing-out arm system for feeding the rack by pushing out a rear end portion of the rack. In addition, it is preferable to provide a storage unit which stores an analysis result by monitoring the analysis result of the control unit for determining whether or not the retest is needed and each unit.

Advantageous Effects of Invention

According to the present invention, the following advantageous effects can be expected.

1) If a biochemical analysis unit and a clotting-time analysis unit are combined and integrated with each other, advantageous effects can be expected in that specimen management flow is improved and device management is simplified.

2) The biochemical analysis unit measures the synthetic substrate item/latex agglutination item in which a reaction time is predetermined for every item in the blood coagulation test items, and the clotting-time analysis unit measures the clotting-time item in which the reaction time varies depending on each sample. In this manner, a time for awaiting the specimen rack due to an uncertain reaction time is shortened, thereby leading to facilitated scheduling and an improved throughput of the overall device. Furthermore, the synthetic substrate item/latex agglutination item whose reaction time is longer than that of the clotting-time item is measured by the biochemical analysis unit which has a more improved throughput than the clotting-time analysis unit. Accordingly, it is possible to expect a considerably improved throughput in measuring the blood coagulation test items.

3) The clotting-time analysis unit no longer needs to measure the synthetic substrate item/latex agglutination item. Accordingly, it is possible to reduce the number of measurement ports of the clotting-time analysis unit, thereby enabling the device cost to be reduced. Moreover, the biochemical analysis unit of a turntable system including a reaction vessel cleaning mechanism measures the synthetic substrate item/latex agglutination item in the blood coagulation test items. It is possible to reduce the consumption of disposable reaction vessels for the blood coagulation test items, thereby leading to reduced life-cycle costs.

4) The retest can be performed in random order from the clotting-time item whose retest is determined. Therefore, a shortened turnaround time or an improved throughput can be expected.

An object of the present invention is to provide an automatic analysis device in which a biochemical analysis unit and a blood coagulation analysis unit are integrated with each other and which has an improved throughput while the device cost and the life-cycle cost are reduced.

DESCRIPTION OF EMBODIMENTS

Figure 1:
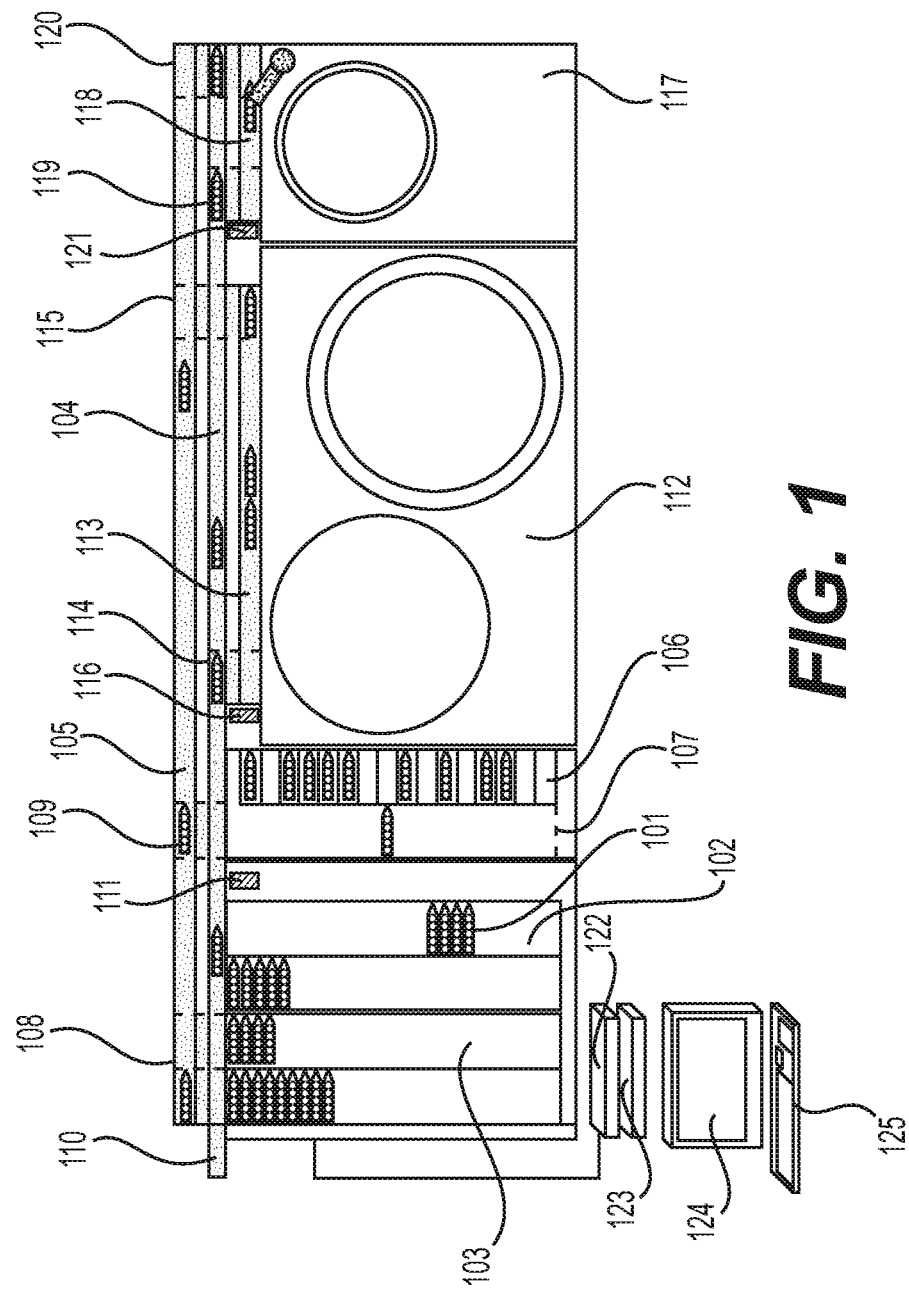
FIG. 1 is a schematic view of an automatic analysis device including a biochemical analysis unit and a clotting-time analysis unit which employs a turntable system according to an embodiment of the present invention.

Hereinafter, an embodiment of the present invention will be described in detail with reference to the drawings. In principle, the same reference numerals will be given to those which have the same function in all of the drawings for describing the present embodiment, and repeated description thereof will be omitted as much as possible.

Hereinafter, in the present specification, in some cases, a synthetic substrate item or a latex item in a blood coagulation test item is referred to as a first test item, and a clotting-time item is referred to as a second test item. In addition, in some cases, a biochemical measurement item is referred to as a third test item. An example of the first test item includes D-dimer, FDP, SFMC, and PIC. An example of the second test item includes PT, APTT, and Fbg. An example of the third test item includes ALT and AST.

FIG. 1 is a schematic view of an automatic analysis device including a biochemical analysis unit and a clotting-time analysis unit which employs a turntable system according to an embodiment of the present invention. As an example of configuration elements of a conveyance system for conveying a specimen rack 101 on which a specimen container accommodating a sample such as analysis-targeted blood and urine is mounted, FIG. 1 illustrates a rack supply unit 102, a rack accommodation unit 103, a conveyance line 104 which conveys the specimen rack 101 to the analysis unit, a return line 105, a rack standby unit 106, a standby unit handling mechanism 107, a rack returning mechanism 108, a rack distributing mechanism 109, a rack loading unit for urgent specimen 110, and a reading unit (conveyance line) 111.

A conveyance system of a biochemical analysis unit 112 arranged along the conveyance line 104 includes a reading unit (biochemistry) 116 which collates analysis request information on a sample accommodated in the specimen rack 101 from the conveyance line 104, a rack conveying mechanism (biochemistry) 114 which receives the specimen rack 101 from the conveyance line 104, a dispensing line (biochemistry) 113 which has a function to cause the specimen rack 101 to stand by until dispensing starts and which dispenses the sample inside the specimen container of the specimen rack 101, and a rack handling mechanism (biochemistry) 115 which conveys the specimen rack 101 which completed sample dispensing to the conveyance line 104 or the return line 105.

A conveyance system of a clotting-time analysis unit 117 arranged along the conveyance line 104 includes a reading unit (clotting) 121 which collates analysis request information on the sample accommodated in the specimen rack 101 from the conveyance line 104, a rack conveying mechanism (clotting) 119 which receives the specimen rack 101 from the conveyance line 104, a dispensing line (clotting) 118 which has a function to cause the specimen rack 101 to stand by until dispensing starts and which dispenses the sample inside the specimen container of the specimen rack 101, and a rack handling mechanism (clotting) 120 which conveys the specimen rack 101 which completed sample dispensing to the return line 105. The dispensing line (clotting) 118 includes a specimen rack conveying mechanism which can move the specimen rack 101 forward and rearward in a travelling direction of the specimen rack 101. In order to prevent the specimen rack 101 from being jammed, when the analysis units are arranged, it is desirable that the biochemical analysis unit 112 which generally has an excellent specimen throughput is arranged on an upstream side of the clotting-time analysis unit 117. In addition, the automatic analysis device according to the present embodiment includes a control unit 122, a storage unit 123, a display unit 124, and an input unit 125.

The biochemical analysis unit 112 adopts a known configuration, and mainly includes a specimen probe which aspirates a specimen from the specimen rack 101, a reaction cell which discharges the aspirated specimen, a reagent storage which stores a reagent to be mixed with the specimen inside the reaction cell, a regent dispensing mechanism which discharges the reagent to the reaction cell, an optical system including a detector and its light source, which measures transmitted light or scattered light by emitting light to a mixture solution of the specimen and the reagent inside the reaction cell, and an arithmetic unit which calculates predetermined component density contained in the mixture solution, based on data obtained from the detector. The biochemical analysis unit 112 can analyze at least the third test item.

In addition, the clotting-time analysis unit 117 adopts a known configuration, and mainly includes a specimen probe which aspirates the specimen from the specimen rack 101, a reaction vessel which discharges the aspirated specimen, a reagent storage which holds the reagent to be mixed with the specimen inside the reaction vessel, a regent dispensing mechanism which discharges the reagent to the reaction vessel, an optical system including a detector and its light source, which measures transmitted light or scattered light by emitting light to a mixture solution of the specimen and the reagent inside the reaction cell, and an arithmetic unit which calculates a clotting-time of the specimen, based on data obtained from the detector. The clotting-time analysis unit 117 can analyze at least the second test item.

Figure 2:
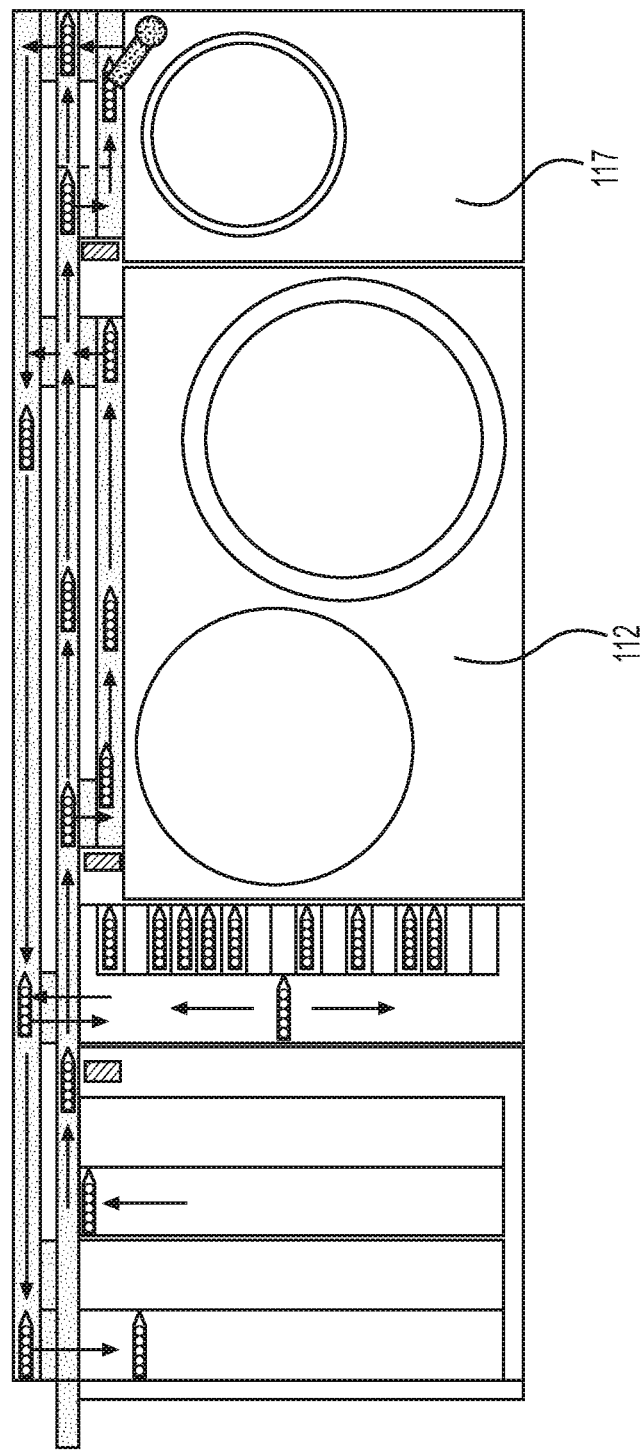
FIG. 2 is a schematic view illustrating a conveyance path of a specimen rack according to the embodiment of the present invention.
Figure 4:
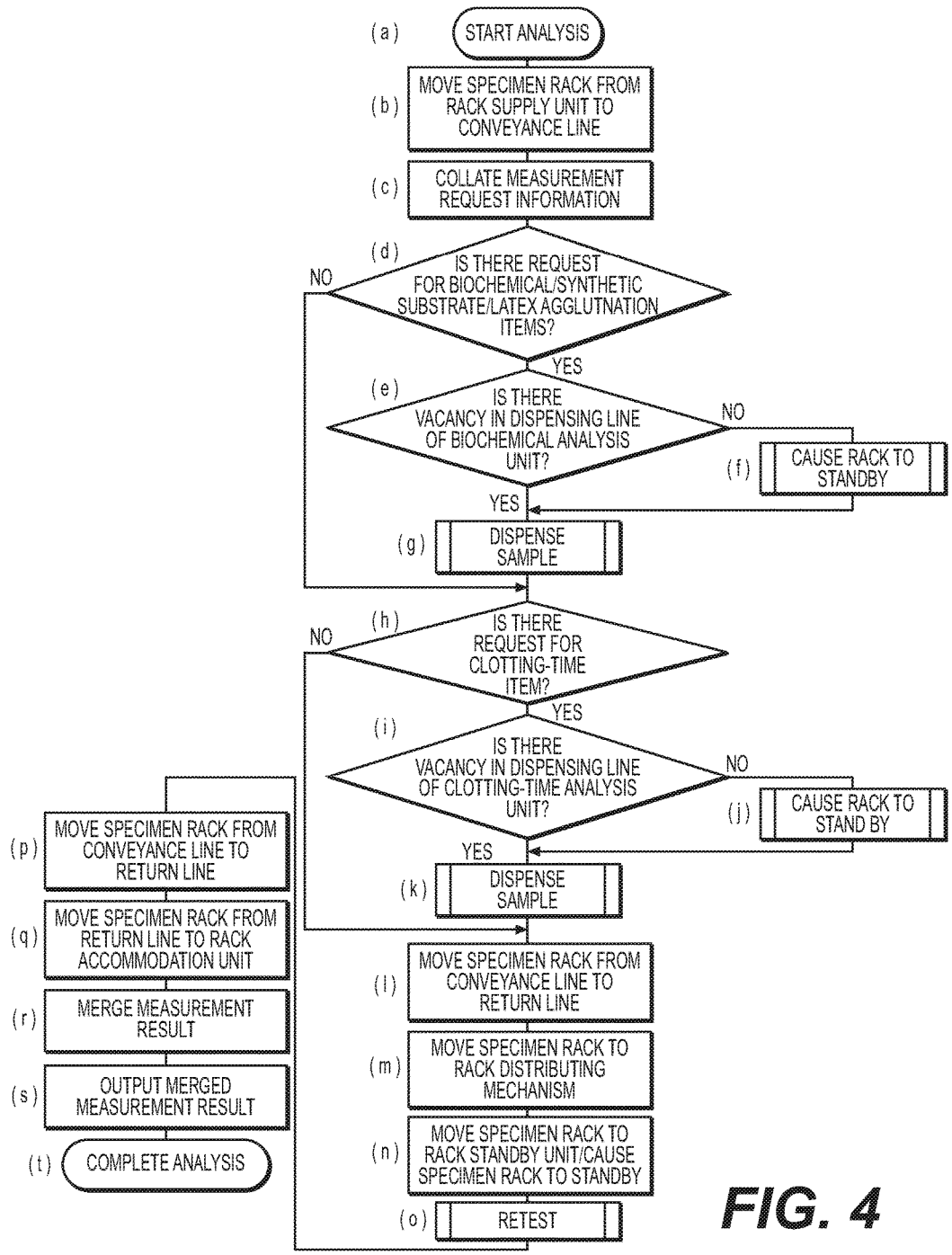
FIG. 4 is a flowchart illustrating an analysis operation according to the embodiment of the present invention.
Figure 5:
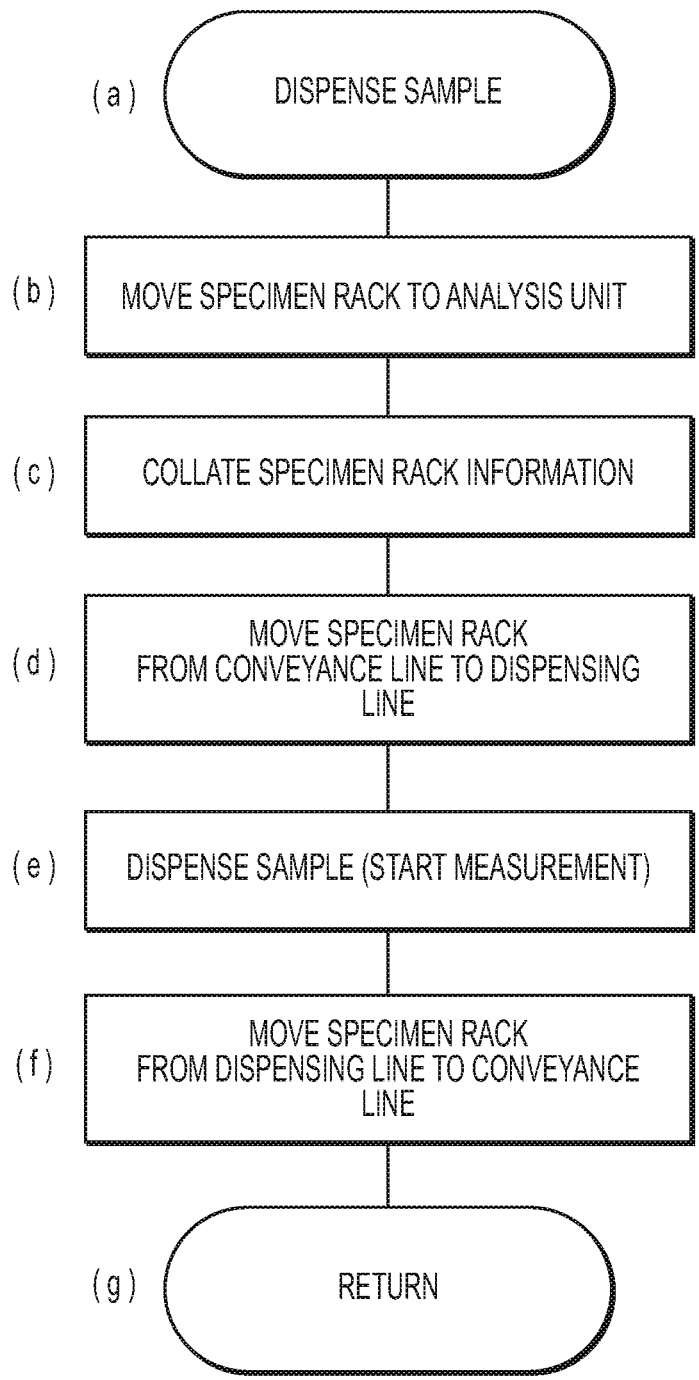
FIG. 5 is a flowchart illustrating a sample dispensing operation of an analysis unit according to the embodiment of the present invention.
Figure 6:
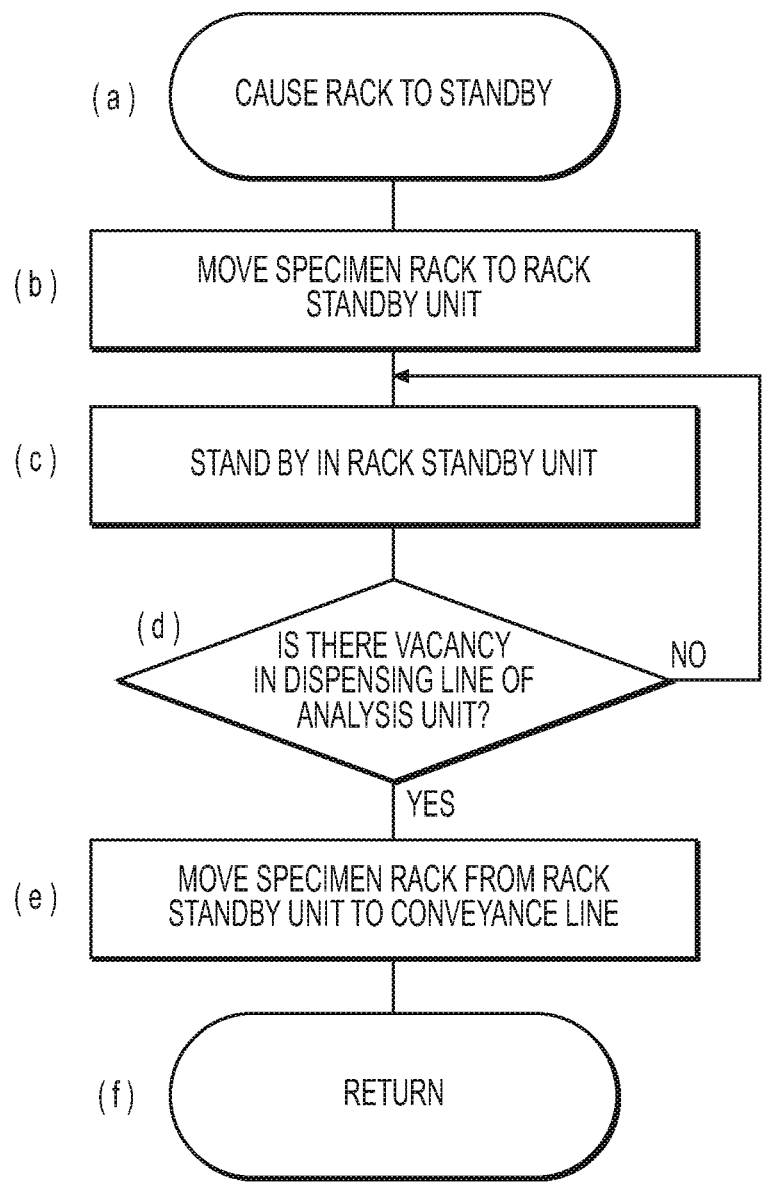
FIG. 6 is a flowchart illustrating a rack standby operation in a rack standby unit according to the embodiment of the present invention.

FIG. 2 is a schematic view illustrating a conveyance path of the specimen rack 101. The conveyance path of the specimen rack 101 during analysis will be described with reference to FIG. 2, FIG. 4 illustrating a flowchart of an analysis operation, FIG. 5 illustrating a flowchart of a sample dispensing operation, and FIG. 6 illustrating a flowchart of a rack standby operation in the rack standby unit 106.

If the input unit 125 requests for an analysis, the analysis starts (FIG. 4a), and the control unit 122 moves the specimen racks 101 arrayed in parallel in the rack supply unit 102 to the conveyance line 104 (FIG. 4b). Thereafter, the reading unit (conveyance line) 111 reads an identification medium such as a bar code label adhering to the specimen rack 101 and the sample container to be accommodated in the specimen rack 101, thereby identifying a specimen rack number and a sample container number. The specimen rack number and the sample container number which are identified by the reading unit (conveyance line) 111 are transmitted to the control unit 122. The control unit 122 associates a type of the specimen rack 101 and a type of analysis items instructed to each sample container with a specimen receiving number, and collates the types with measurement request information instructed in advance from the input unit 125 (FIG. 4c). Based on a referred result thereof, the destination of the specimen rack 101 is determined by the control unit 122, and is stored in the storage unit 123 so as to be used in the subsequent processing of the specimen rack 101.

The biochemical analysis unit 112 includes a reaction disk for promoting a reaction between a sample and a reagent which correspond to various analysis items inside each reaction vessel circumferentially arranged in parallel, a reagent disk which is operated so that the reagent corresponding to the various analysis items is located at a reagent aspirating position, a sample dispensing mechanism which dispenses the sample inside the sample container to a reaction vessel on the reaction disk from the dispensing line (biochemistry) 113, and a reagent dispensing mechanism which dispenses the reagent corresponding to the analysis item from a reagent bottle on the reagent disk to the reaction vessel on the reaction disk.

The control unit 122 confirms whether there is a measurement request for any one of biochemical, synthetic substrate, and latex agglutination items (FIG. 4d). In a case where the sample whose analysis is requested by the biochemical analysis unit 112 is present, the control unit 122 confirms whether the dispensing line (biochemistry) 113 is vacant (FIG. 4e). If there is a vacancy, the control unit 122 conveys the specimen rack 101 to the biochemical analysis unit 112, and starts to dispense the sample (FIG. 4g). On the other hand, if there is no vacancy in the dispensing line (biochemistry) 113, the control unit 122 controls the standby unit handling mechanism, and moves the specimen rack 101 to the rack standby unit 106 so that the specimen rack 101 stands by at that place (FIG. 4f).

Next, rack standby (FIG. 4f) will be described with reference to FIG. 6. After the control unit 122 moves the specimen rack 101 to the rack standby unit 106 (FIGS. 6a to 6c), the control unit 122 frequently confirms whether the dispensing line of the analysis unit is vacant (FIG. 6d). In a case where there is no vacancy, the specimen rack 101 is caused to stand by in the rack standby unit 106. In a case where there is a vacancy, the control unit 122 moves the specimen rack 101 from the rack standby unit 106 to the conveyance line (FIG. 6e). That is, the specimen rack 101 stands by until the dispensing line (biochemistry) 113 is vacant.

Next, sample dispensing (FIG. 4g) will be described with reference to FIG. 5. For the specimen rack 101 conveyed to the biochemical analysis unit 112, the reading unit (biochemistry) 116 collates specimen rack information (FIG. 5b), thereby collating analysis information. The control unit 122 controls the rack conveying mechanism (biochemistry) 114 so as to move from above the conveyance line 104 to the dispensing line (biochemistry) 113 (FIG. 5d). The control unit 122 conveys the specimen rack 101 to a dispensing position, and performs a control so that a dispensing nozzle of a specimen dispensing mechanism is inserted into the sample container whose analysis is instructed at the position, the sample is aspirated, and the sample is dispensed to a reaction vessel included in the biochemical analysis unit 112 (FIG. 5e). In a case where a test for two or more items is instructed for the same sample container and in a case where a test item is instructed for the other sample container on the same specimen rack 101, a sample collecting operation is successively and repeatedly performed. The control unit 122 moves the specimen rack 101 in which the sample collecting operation is completed for all analysis items instructed with regard to the biochemical analysis unit 112 from the dispensing position to a corresponding position of the rack handling mechanism (biochemistry) 115. Thereafter, the control unit 122 moves the specimen rack 101 from the dispensing line to the conveyance line 104 (FIG. 5f). Alternatively, the control unit 122 moves the specimen rack 101 from the dispensing line to the return line 105 as will be described later.

Next, the control unit 122 confirms whether there is a request for the clotting-time item to be analyzed by the clotting-time analysis unit in the sample mounted on the specimen rack 101 (FIG. 4h). In a case where the sample is present in which the analysis performed by the clotting-time analysis unit 117 is requested, the control unit 122 confirms whether the dispensing line (clotting) of the clotting-time analysis unit 117 is vacant (FIG. 4i). If there is a vacancy, the specimen rack 101 is conveyed to the clotting-time analysis unit 117 so as to start the sample dispensing (FIG. 4k). The same control as that in FIG. 5 is performed, and thus, details thereof will be omitted. On the other hand, in a case where there is no vacancy in the dispensing line (clotting) 118 (FIG. 4j), the specimen rack 101 is transferred to the return line 105 by the rack handling mechanism (biochemistry) 115, and is moved to the rack standby unit 106 via the rack distributing mechanism 109 by the standby unit handling mechanism so as to stand by until the dispensing line (clotting) 118 is vacant. The same control as that in FIG. 6 is performed, and thus, details thereof will be omitted.

The specimen rack 101 in which the sample collecting operation is completed for all analysis items instructed with regard to the clotting-time analysis unit 117 is moved to a corresponding position of the rack handling mechanism (clotting) 120, and is transferred to the return line 105 by the rack handling mechanism (clotting) 120 (FIG. 4l). The control unit 122 causes the return line 105 to convey the specimen rack 101 to the rack distributing mechanism 109 (FIG. 4m).

In a case where there is no request for the analysis to be performed by the clotting-time analysis unit 117, the specimen rack 101 is transferred onto the return line 105 by the rack handling mechanism 118. Thereafter, the specimen rack 101 is conveyed to the rack distributing mechanism 109 (FIG. 4m).

The storage unit 123 stores the specimen rack number of the specimen rack 101 in which the sample collecting is completed and which is conveyed to the rack distributing mechanism 109. Accordingly, the control unit 122 previously determines whether the specimen rack 101 does not need a retest, such as a rack for control specimen, a rack for a standard specimen, and a rack for a cleaning solution, or whether the specimen rack 101 has a possibility of the retest. If the retest is not needed, based on the determination, the specimen rack 101 is transferred by the rack distributing mechanism 109 which receives a control signal of the control unit 122 to the rack returning mechanism 108, and is accommodated in the rack accommodation unit 103 by the rack returning mechanism 108. If the specimen rack 101 has the possibility of the retest, the specimen rack 101 is received by the standby unit handling mechanism 107, and is delivered to the rack standby unit 106 so as to stand by until it is determined whether or not the retest is needed (FIG. 4n).

On the other hand, the sample collected into the reaction vessel of each analysis unit is caused to react with the reagent dispensed by the reagent dispensing mechanism, and data corresponding to each measured analysis item is output to the control unit 122. The control unit 122 collates preset determination reference and analysis test data. In a case where measurement data is not proper, the control unit 122 causes the storage unit 123 to store the specimen that needs the retest after associating the specimen rack number and the sample container number with each other, thereby performing the retest (FIG. 4o). For example, the case where the measurement data is not proper includes a case where the measurement data is beyond or below the preset determination reference. The specimen rack 101 whose retest is completed is transferred from the rack standby unit 106 to the return line 105 by the standby unit handling mechanism 107 (FIG. 4p). The specimen rack 101 is conveyed to the rack returning mechanism 108 by the return line 105, and is accommodated into the rack accommodation unit 103 by the rack returning mechanism 108 (FIG. 4q). Analysis test data for the first time and analysis test data of the retest are merged by the control unit 122 (FIG. 4r), and are displayed on the display unit 124 (FIG. 4s), thereby completing the analysis (FIG. 4t).

Figure 3:
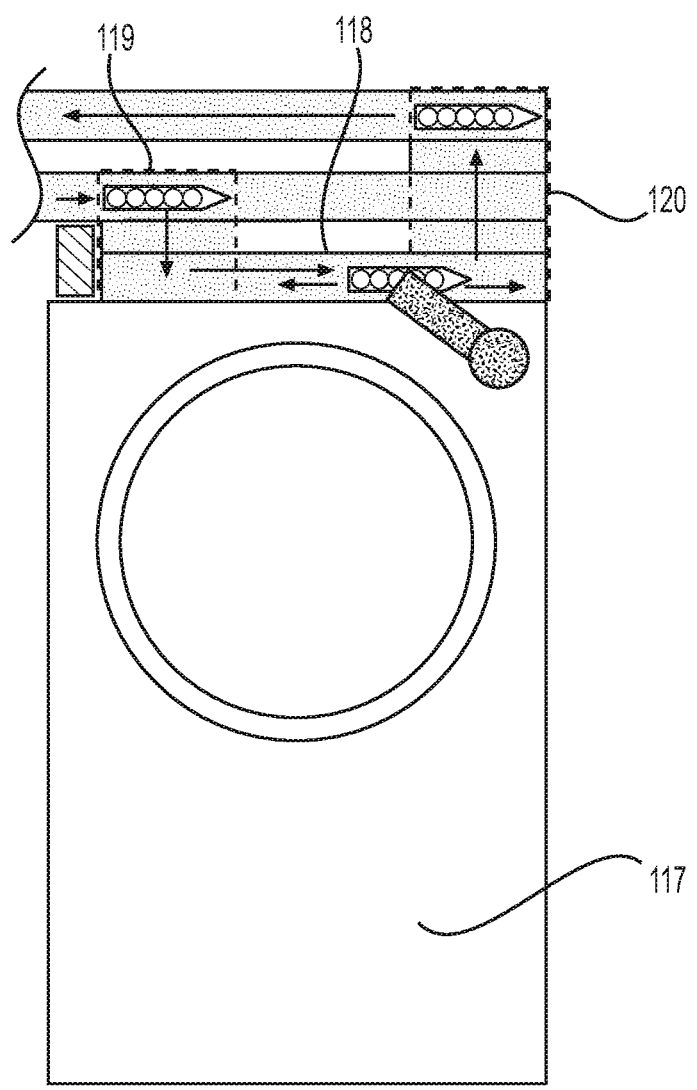
FIG. 3 is a schematic view illustrating an operation of the specimen rack in a dispensing line of the clotting-time analysis unit according to the embodiment of the present invention.

FIG. 3 is a schematic view illustrating an operation of the specimen rack 101 of the dispensing line (clotting) 121 in the clotting-time analysis unit 117 according to the embodiment of the present invention. The dispensing line (clotting) 118 includes a specimen rack conveying mechanism which can move the specimen rack 101 forward and rearward in the travelling direction. A sampling mechanism can have an access to the specimen on the specimen rack 101 at random order. Accordingly, the retest can be performed at random order in a case of the clotting-time item in which a reaction time varies depending on the specimen. For example, if it is assumed that specimen containers A, B, C, D, and E are arrayed in parallel from the front in the travelling direction of the specimen rack 101, the automatic analysis device disclosed so far has a sequential access to the specimen containers A, B, C, D, and E. However, the random order means that the sampling mechanism is not limited to this sequence and can have an access to any sequence such as the sequence of the specimen containers C, B, A, E, and D. That is, as illustrated by an arrow in FIG. 3, the specimen rack 101 can be moved rearward in the travelling direction. For example, the control unit 122 moves the dispensing line (clotting) 118 in the opposite direction. In this manner, the control unit 122 can move the specimen rack 101 rearward in a direction opposite to the travelling direction, and the sampling mechanism can have a sequential access to the specimen containers C, B, E, and D.

Hereinafter, a controlling operation according to the present invention in a case where the retest is performed will be described. In the following description, a case will be described where there is a measurement request for the specimen container mounted on one specimen rack 101 in both the biochemical analysis unit 112 and the clotting-time analysis unit 117, and where the measurement data measured by both of these is a retest target. This case is considered to include two cases such as a case where the retest of the clotting-time item precedes and a case where the retest of the biochemical item precedes. Both of these have controlling methods which are different from each other. Accordingly, description will be made by separating the cases from each other. The following control is not limited to a case where both items of the biochemical analysis unit 112 and the clotting-time analysis unit 117 are measured for the same specimen container. For example, according to the previous example, the specimen container A includes only a test for the biochemical item, and the specimen container B includes only a test for the clotting-time item.

Figure 7:
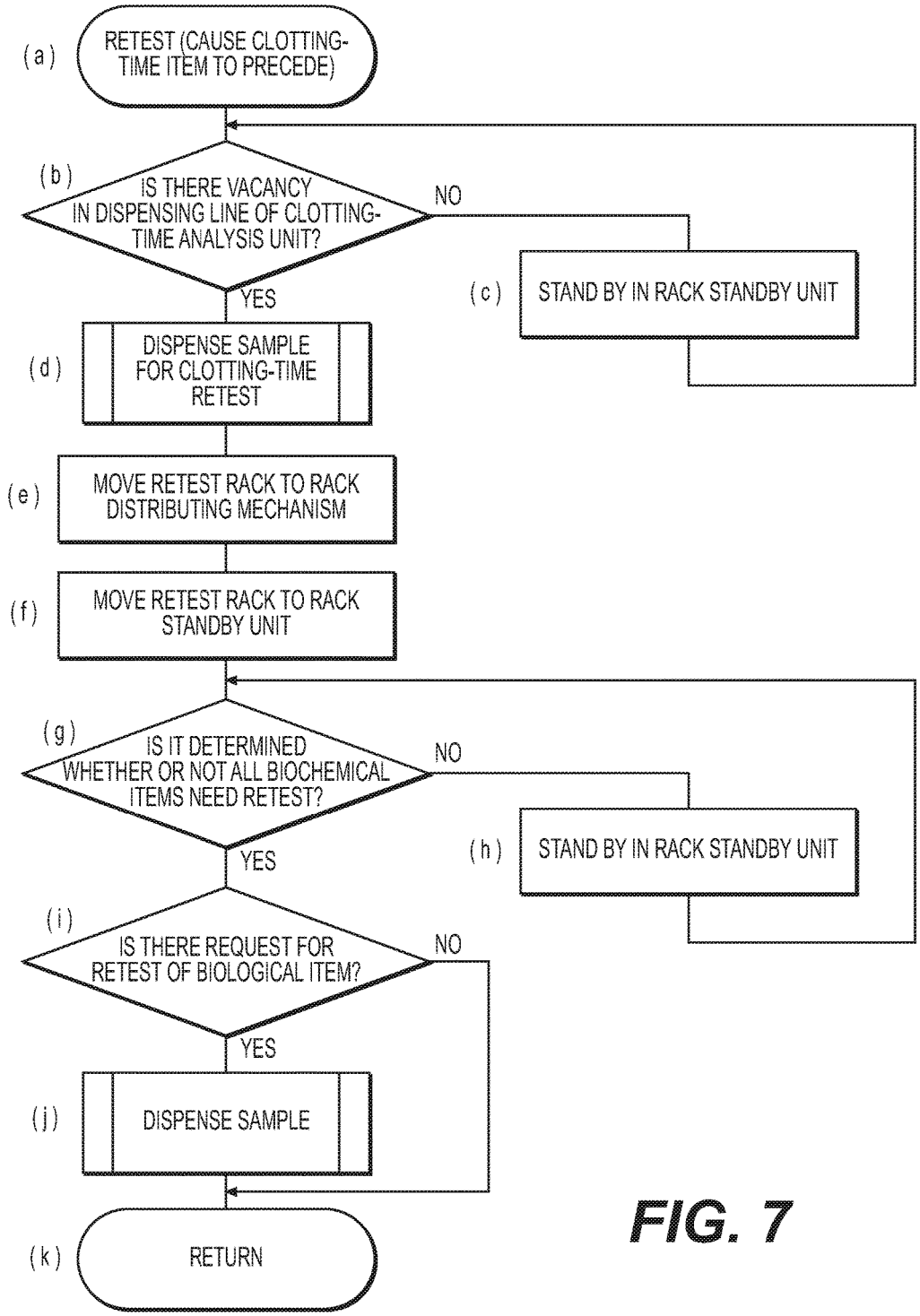
FIG. 7 is a flowchart illustrating a system operation in a case where a retest of a clotting-time item according to the embodiment of the present invention is performed beforehand.
Figure 9:
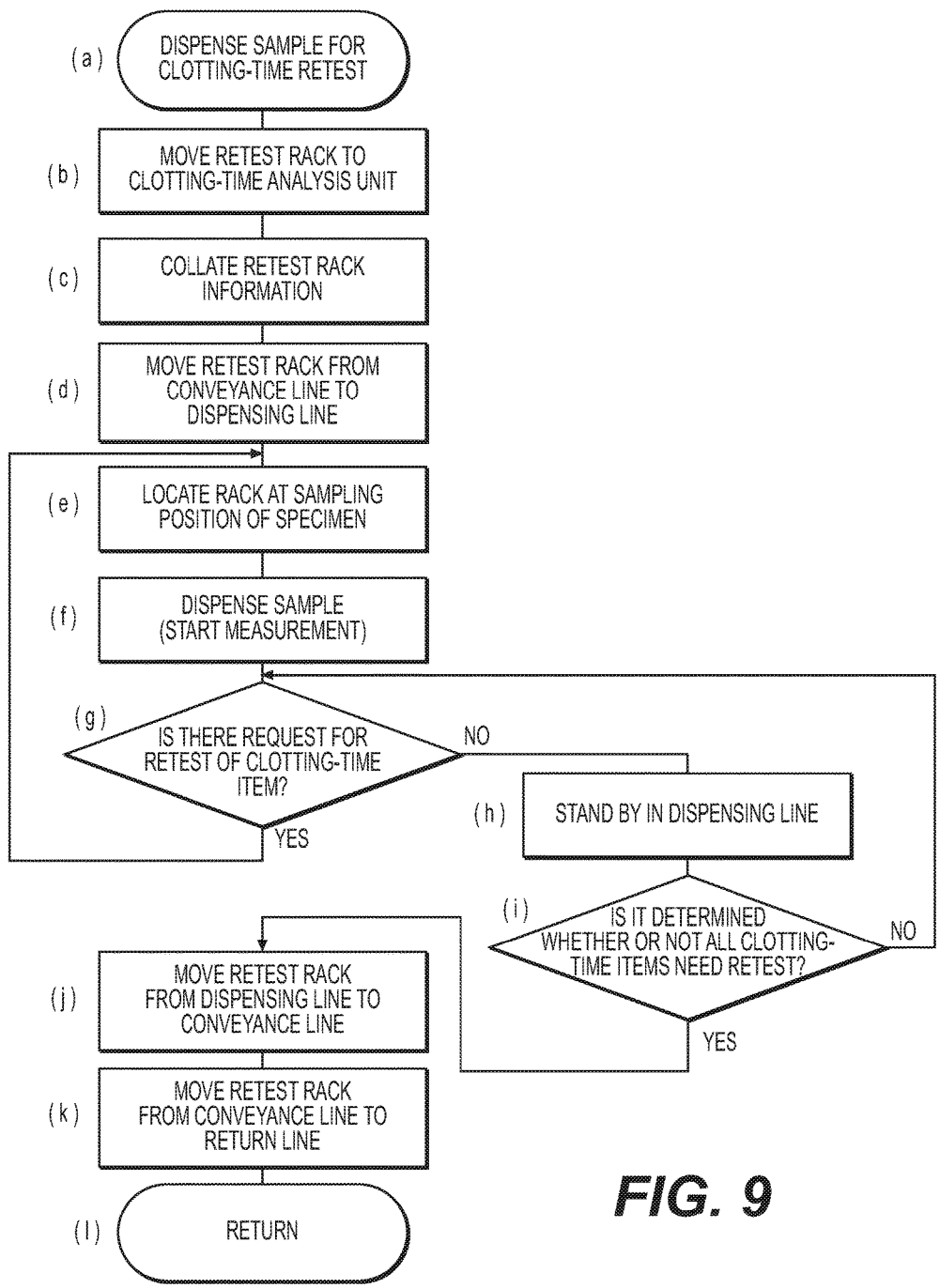
FIG. 9 is a flowchart illustrating a sample dispensing operation in the clotting-time analysis unit during the retest according to the embodiment of the present invention.

A system operation during the retest in a case where the retest of the clotting-time item precedes will be first described with reference to FIGS. 7 and 9. In a case where based on the measurement result of the clotting-time analysis unit 117 prior to the biochemical analysis unit 112, an item which is determined to need the retest by the control unit 122 is present in a sample of the specimen rack 101, the control unit 122 confirms whether the dispensing line (clotting) 118 is vacant (FIG. 7b). If there is a vacancy, the specimen rack 101 is conveyed to the clotting-time analysis unit 117, thereby starting to dispense the sample (FIG. 7d).

In a case where there is no vacancy in the dispensing line (clotting) 118, the specimen rack 101 remains unchanged and stands by in the rack standby unit 106 until the dispensing line (clotting) 118 is vacant (FIG. 7c).

Here, sample dispensing (FIG. 7(d)) during the retest of the clotting-time item will be described in detail with reference to FIG. 9. First, the control unit 122 moves the retest rack 101 including a retest sample to the clotting-time analysis unit 117 (FIG. 9c). Here, it is desirable that the control unit 122 controls the conveyance line so as to convey the specimen rack from the standby unit 106 to the dispensing line (clotting) 118 when an item which needs the retest is determined for the first time in the clotting-time item in the same specimen rack 112. For example, in a case where the clotting-time of PT, APTT, and Fbg is measured with regard to the sample container in the specimen rack, and in a case where PT among these items is determined as the item which needs the retest for the first time, the conveyance of the specimen rack starts even though the measurement result of the clotting-time of APTT and Fbg is not completed. This can shorten a time required before the clotting-time is retested.

The control unit 122 uses the reading unit (clotting) 121 so as to read an identification medium such as a bar code label adhering to the moved specimen rack 101. Based on the read information, the control unit 122 collates retest specimen rack information in order to confirm whether the moved specimen rack 101 includes a retest-targeted specimen container (FIG. 9c). The control unit 122 causes the rack conveying mechanism (clotting) 119 to transfer the specimen rack 101 recognized as a correct specimen rack by the collation from above the conveyance line 104 to the dispensing line (clotting) 118 (FIG. 9d). The control unit 122 causes the specimen rack conveying mechanism of the dispensing line (clotting) 121 to move the specimen rack 101 so that the sample container whose retest is instructed is located at a sampling position of the specimen dispensing mechanism (FIG. 9e). Then, sample dispensing is performed (FIG. 9f).

The control unit 122 confirms whether there is a retest request for the clotting-time item in the other sample container of the same specimen rack 101 (FIG. 9g). In a case where there is the other retest request, the specimen rack 101 is moved so that the successively corresponding sample container is located at a sampling position of the specimen dispensing mechanism, and a sample collecting operation is repeatedly performed. For example, if the successively corresponding sample container is located on the downstream side in the travelling direction of the specimen rack 101, the specimen rack 101 is moved rearward in the travelling direction, and the sample collection operation is performed on the sample container. On the other hand, if the successively corresponding sample container is located on the upstream side in the travelling direction of the specimen rack 101, similarly to the normal movement of the specimen rack, the specimen rack 101 is moved forward in the travelling direction, and the sample collection operation is performed on the sample container. The specimen rack conveying mechanism may be the dispensing line itself, or may be a mechanism separate from the dispensing line.

That is, the control unit 122 controls a position of the specimen rack in the dispensing line (clotting) so as to dispense the sample from the specimen container in the sequence in which the specimen container is determined to need the retest. For example, in a case where the respective clotting-time items PT are measured for the specimen containers A, B, and C in the previous example, and in a case where it is determined that the retest is needed in the sequence of the specimen containers B, A, and C, the sample is dispensed in the sequence of the specimen containers B, A, and C.

In this manner, it is possible to perform the retest having an excellent throughput.

On the other hand, in a case where there is no request for the other retest, the specimen rack 101 is controlled so as to stand by in the dispensing line (clotting) 118 until it is determined whether or not all clotting-time items in the specimen rack 101 need the retest (FIG. 9h). Even in a case where there is no request for the other retest, the timing when the measurement result of the clotting-time item can be obtained varies. Accordingly, in some cases, there may be a retest request for the sample container to be included in the specimen rack 101 afterwards. Therefore, the specimen rack 101 is caused to stand by so that the sample can be quickly dispensed for this retest request.

The control unit 122 periodically confirms whether or not all clotting-time items are determined to need the retest for the sample container of the specimen rack 101. In a case where all are not determined based on the confirmation result, the confirmation in FIG. 9g is performed. In a case where all are determined, the process proceeds to the subsequent flow. Whether or not the retest is needed cannot be determined if the measurement result of the clotting-time item to be included in the specimen rack 101 cannot be obtained. Accordingly, in a case where the specimen rack 101 proceeds to the subsequent flow, the specimen rack 101 is limitedly stand by in the dispensing line until the measurement result of all clotting-time items can be obtained.

The control unit 122 moves the specimen rack 101, in which the sample collecting operation is completed for the retest of all clotting-time items, to a corresponding position of the rack handling mechanism (clotting) 120 (FIG. 9j). The control unit 122 causes the rack handling mechanism (clotting) 120 to transfer the specimen rack 101 to the return line 105 (FIG. 9k). The control unit 122 causes the return line 105 to convey the specimen rack 101 to the rack distributing mechanism 109 (FIG. 7e).

If the specimen rack 101 has a possibility of the retest for the biochemical items, the control unit 122 delivers the specimen rack 101 to the standby unit handling mechanism 107 so as to be conveyed to the rack standby unit 106 (FIG. 7f). The control unit 122 confirms whether or not all biochemical items are determined to need the retest. In a case where it is confirmed that all biochemical items are not determined to need the retest, the specimen rack 101 stands by in the rack standby unit 106 (FIG. 7h). In a case where all biochemical items are determined to need the retest, the control unit 122 confirms whether there is a retest request for the biochemical item (FIG. 7i). That is, the control unit 122 collates preset determination reference and analysis test data. In a case where the measurement data is not proper based on the collation result, the control unit 122 causes the storage unit 123 to store the specimen that needs the retest after associating the specimen rack number and the sample container number with each other. For the specimen rack 101 in which the specimen which needs the retest is present based on the confirmation result (FIG. 7i), the sample is dispensed in accordance with the flow illustrated in FIG. 5 (FIG. 7j). In a case of analysis performed by the biochemical analysis unit 112, a measurement time is generally fixed to 10 minutes. Accordingly, the measurement data can be obtained in the sequence in which the sample is dispensed.

Therefore, it is not necessary to dispense the sample at random order as performed by the previously described clotting-time analysis unit.

The specimen rack 101 in which it is determined that the retest is not needed is transferred from the rack standby unit 106 to the return line 105 by the standby unit handling mechanism 107, is conveyed to the rack returning mechanism 108 by the return line 105, and is accommodated in the rack accommodation unit 103 by the rack returning mechanism 108. The analysis test data for the first time and the analysis test data of the retest are merged by the control unit 123, and are displayed on the display unit 124, thereby completing the analysis.

The present embodiment aims to shorten a turnaround time by causing the clotting-time analysis unit to perform sampling in random order before it is determined whether or not all clotting-time items need the retest. In the present specification, this retest mode is described as a clotting real-time retest mode. The clotting real-time retest mode is an effective retest method in a case where the measurement request of the clotting-time item (second test item) is sparse and intermittent compared to the biochemical measurement item (third test item) or the synthetic substrate/latex agglutination item (first test item) (for example, in a case where the measurement request for the specimen rack is intermittent one by one). In addition, an embodiment is also conceivable in which scheduling is facilitated by performing the retest after it is determined whether or not all clotting-time items need the retest.

Hitherto, an example has been described in which the control unit conveys the specimen rack to the dispensing line (clotting) when determining the item which needs the retest in the clotting-time item for the first time. However, as another embodiment, it is also conceivable that the retest is performed after the control unit awaits determination on whether or not all clotting-time items of the same specimen rack need the retest. For example, the control unit can control the conveyance line so as to convey the test rack to the dispensing line (clotting) in a case where a completion time of aspirating the specimen for the retest of the clotting-time item of the specimen rack is earlier than a time required until it is determined whether or not all synthetic substrate items or latex agglutination items (first test items), and biochemical measurement items (third test items) need the retest, when it is determined whether or not all test items of the clotting-time item (second test item) in the same specimen rack need the retest. In the present specification, this retest mode is described as a clotting batch retest mode. Even in this case, the retest can be more quickly performed compared to a case where the specimen is aspirated in the sequence of the biochemical analysis unit and the clotting-time analysis unit. The clotting batch retest mode is an effective method in a case where there is a measurement request for the clotting-time items (second test items) which are more or less united in a lump sum (for example, in a case where several specimen racks are consecutively united).

In addition, an embodiment is also conceivable in which the control unit 122 automatically switches between the clotting real-time retest mode and the clotting batch retest mode in accordance with a measurement request status of the test item. For example, the control unit 122 can automatically switch the retest mode in accordance with the request status of the measurement item stored in the storage unit 123 after the consecutive number of specimens in which the clotting-time item (second test item) is requested is set in advance as a reference value of switching the retest mode. As described above, in the present specification, the retest mode in which the clotting real-time retest mode and the clotting batch retest mode are automatically switched therebetween is described as a clotting automatic retest mode.

Figure 10:
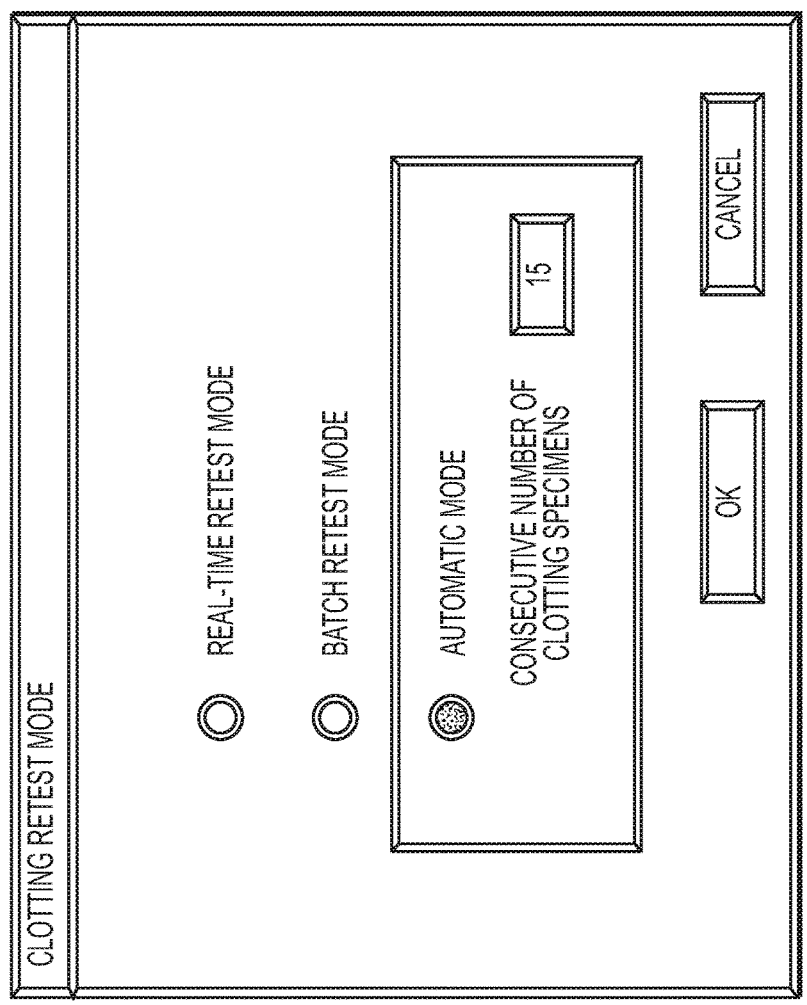
FIG. 10 illustrates a screen for selecting a retest mode of the clotting-time item according to the embodiment of the present invention.

FIG. 10 illustrates a screen for selecting the retest mode of the clotting-time item according to the embodiment of the present invention. In accordance with an operation status of the automatic analysis device, an operator can optionally select the clotting real-time retest mode, the clotting batch retest mode, and the clotting automatic retest mode from a retest condition setting screen of the clotting-time item of the display unit 124. In addition, in the clotting automatic retest mode, the operator can optionally set the consecutive number of specimens in which the clotting-time item (second test item) serving as the reference value of switching the retest mode is requested.

Figure 8:
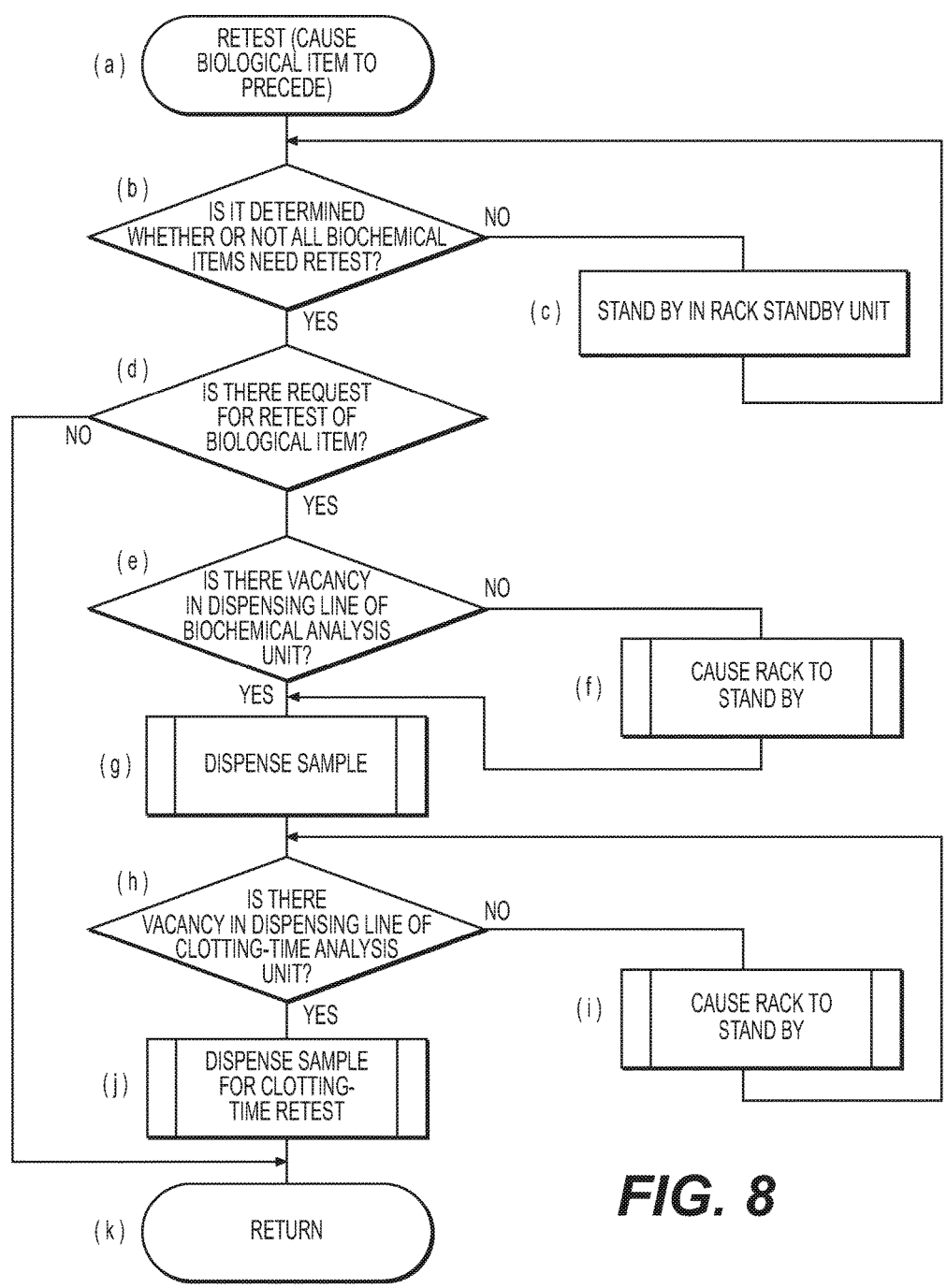
FIG. 8 is a flowchart illustrating a system operation in a case where a retest of a biochemical item according to the embodiment of the present invention is performed beforehand.

Next, a system operation during the retest in a case where the retest of the biochemical item precedes will be described with reference to FIG. 8. Prior to the determination on whether or not the clotting-time item needs the retest for the specimen rack 101 which awaits the retest in the rack standby unit 106, the control unit 122 confirms whether or not it is determined that all biochemical items need the retest (FIG. 8b). If it is not determined, the control unit 122 causes the specimen rack 101 to stand by in the rack standby unit 106 (FIG. 8c). The control unit 122 confirms whether or not there is a retest request for the biochemical item in the specimen rack 101 (FIG. 8d). In a case where there is the biochemical item which needs the retest, the control unit 122 confirms whether or not the dispensing line (biochemistry) 113 is vacant (FIG. 8e). If there is a vacancy, the control unit 122 conveys the specimen rack 101 to the biochemical analysis unit 112, and starts to dispense the sample (FIG. 8g). In a case where the dispensing line (biochemistry) 113 is not vacant, the specimen rack 101 stands by in the rack standby unit 106 until the dispensing line (biochemistry) 113 is vacant, in accordance with the flow illustrated in FIG. 6 (FIG. 8f).

In a case where the retest is determined for the clotting-time item, the control unit 122 confirms whether the dispensing line (clotting) 118 is vacant (FIG. 8h). If there is a vacancy, the control unit 122 conveys the specimen rack 101 to the clotting-time analysis unit 117, and starts to dispense the sample (FIG. 8j). In a case where the dispensing line (clotting) 118 is not vacant, the specimen rack 101 stands by in the rack standby unit 106 until the dispensing line (clotting) 118 is vacant, in accordance with the flow illustrated in FIG. 6 (FIG. 8i). On the other hand, in a case where the dispensing line (clotting) 118 is vacant, the sample is dispensed for the clotting-time retest in accordance with the flow illustrated in FIG. 9.

Here, it is known that when the sample such as serum and plasma is dispensed, a measurement value is influenced by an interference substance such as chyle, hemolysis, and jaundice. Therefore, a technique for calculating a degree of the influence or for correcting the influence is required.

According to the automatic analysis device of the present invention, a photometer mounted on the biochemical analysis unit 112 can calculate a reference value relating to the amount of the interference substance contained in the sample by measuring transmitted light or scattered light.

For example, in a case where the photometer measures absorbance of a mixture solution of the sample and diluent, a degree of the chyle, hemolysis, and jaundice is calculated by using the absorbance of 480 nm, 505 nm, 570 nm, 600 nm, 660 nm, and 700 nm through the following equations.

$$\text{Chyle } (L) = (1/C) \times (\text{absorbance difference between 660 nm and 700 nm})$$

Hemolysis $(H)=(1/A)\times$(absorbance difference between 570 nm and 600 nm$-B\times$absorbance difference between 660 nm and 700 nm)

Jaundice $(I)=(1/D)\times$(absorbance difference between 480 nm and 505 nm$-E\times$absorbance difference between 570 nm and 600 nm$-F\times$absorbance difference between 660 nm and 700 nm)

C, A, D: Coefficient for outputting the absorbance as serum information

B, E, F: Coefficient for correcting overlapped absorption spectra

Furthermore, it is also possible to correct the measurement result in the clotting-time analysis unit 117, based on the reference value relating to the amount of the interference substance.

For example, a reference substance is set in order to calculate the reference value relating to the amount of the interference substance contained in the sample. The biochemical analysis unit 112 and the clotting-time analysis unit 117 measure the reference substance in advance. A correlation curve is obtained between a reference substance measurement result in the biochemical analysis unit 112 and a reference substance measurement result in the clotting-time analysis unit 117, and is stored in the storage unit 123. Prior to the measurement in the clotting-time analysis unit 117, the biochemical analysis unit 112 calculates the reference value relating to the amount of the interference substance contained in the sample. Based on the correlation curve and the reference value which are stored in the storage unit 123, it is possible to correct the measurement result in the clotting-time analysis unit 117.

Figure 11:
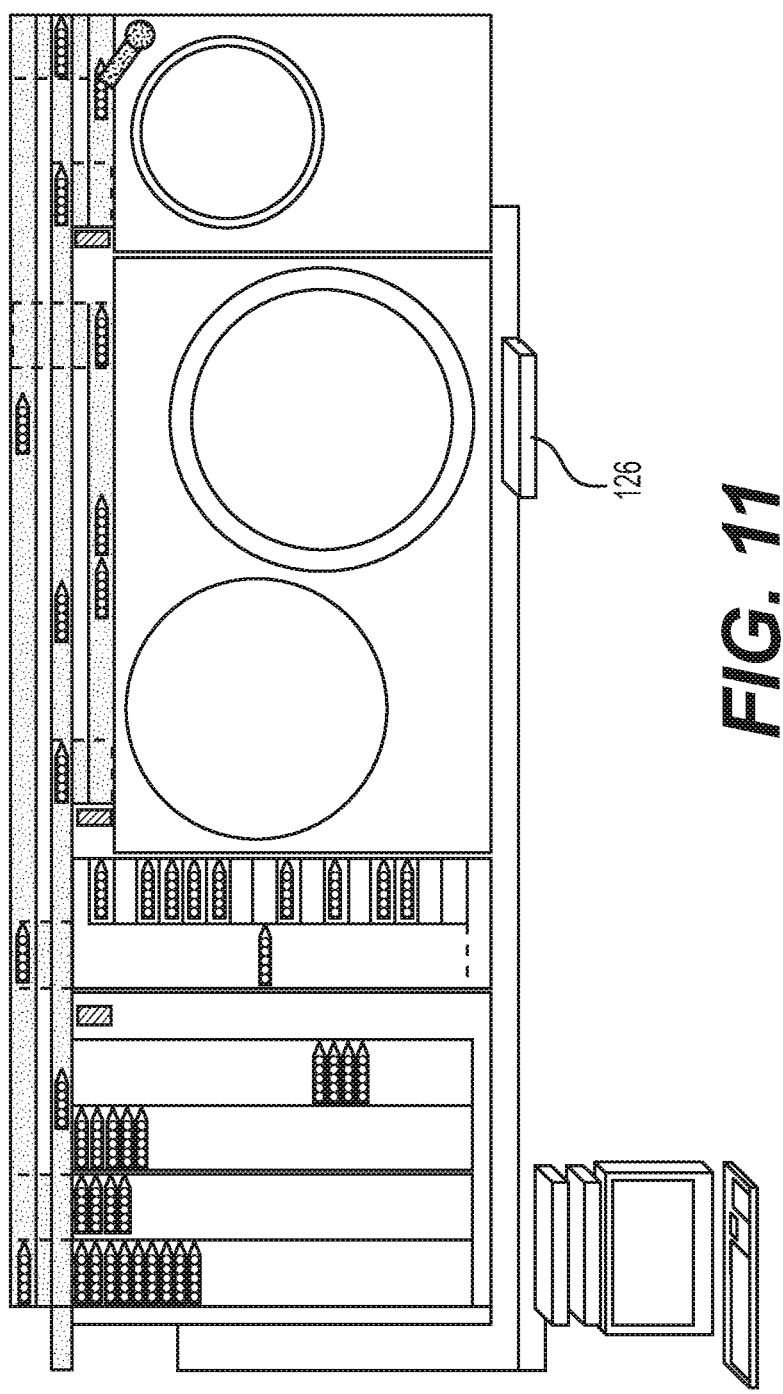
FIG. 11 is a schematic view of the automatic analysis device, which clearly illustrates an amplifier of the clotting-time analysis unit according to the embodiment of the present invention.

In addition, it is also possible to perform amplifier offset control using the reference value. FIG. 11 is a schematic view of the automatic analysis device, which clearly illustrates an amplifier 126 of the clotting-time analysis unit 117 according to the embodiment of the present invention. A detector for detecting transmitted light or scattered light in a measurement port and the amplifier 126 for amplifying a signal transmitted from the detector are connected to the clotting-time analysis unit 117. The control unit 122 acquires the reference value relating to the amount of the interference substance. Based on the reference value, the control unit 122 can offset a zero level of the amplifier 126 before the detector detects light.

Figure 12:
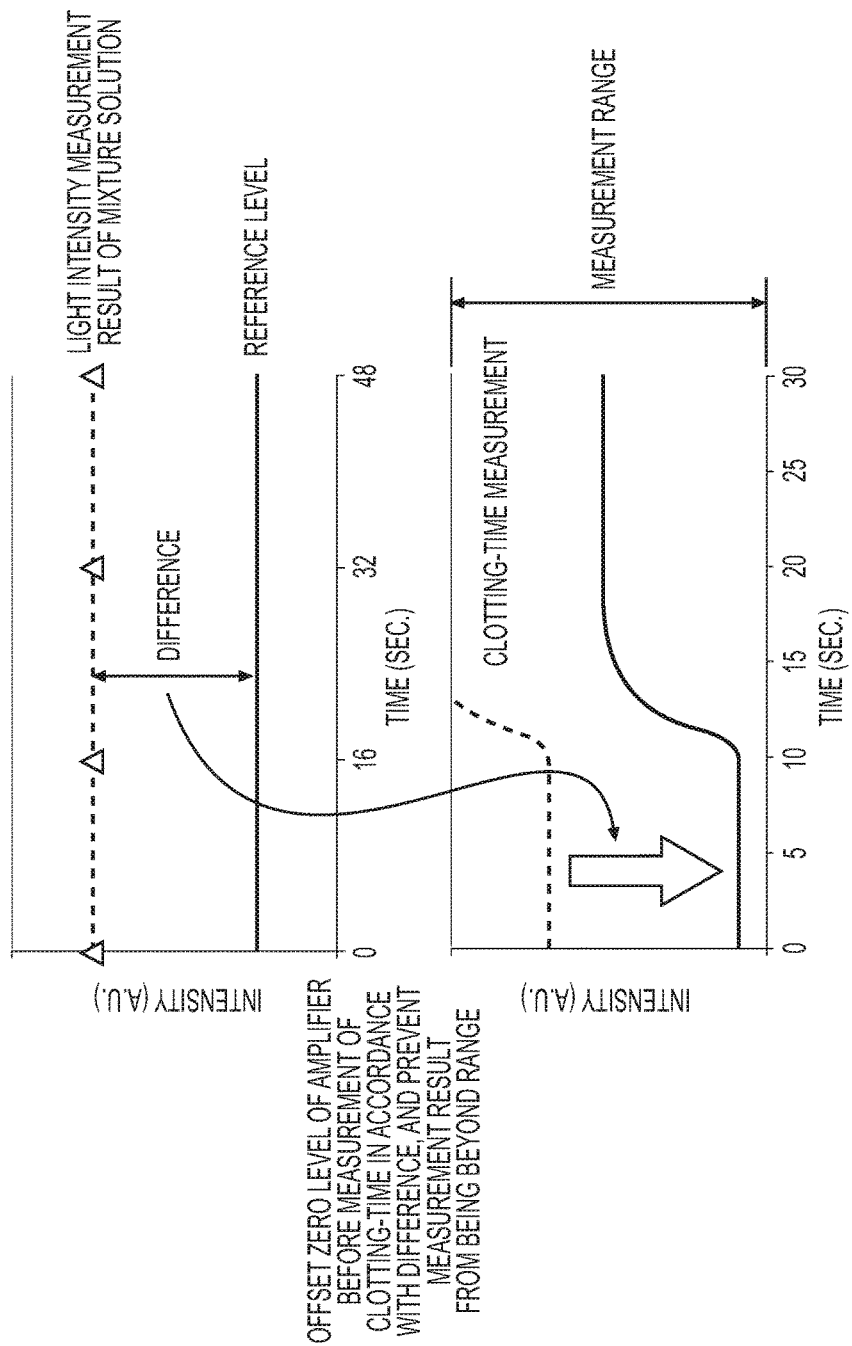
FIG. 12 is a view for describing a function for offsetting a zero level of the amplifier according to the embodiment of the present invention.

FIG. 12 illustrates the measurement result (upper row) of the photometer of the biochemical analysis unit 112 and the measurement result (lower row) of the detector of the clotting-time analysis unit 117. For example, based on a difference between the measurement result of the transmitted light or the scattered light measured by the photometer of the biochemical analysis unit 112 (reference value relating to the amount of the interference substance) and a preset reference level, the control unit 122 controls so as to offset the zero level of the amplifier 126 for amplifying the signal of the detector of the clotting-time analysis unit 117. In this way, based on the measurement result of the biochemical analysis unit 112, the zero level is offset, and the clotting-time analysis unit 117 measures the same sample by using the offset amplifier 126. Accordingly, the measurement is possible by using a suitable amplification factor which prevents the measurement result from falling into an unmeasurable range. This can reduce the unmeasurable frequency, and enables analysis in which the sample or the reagent is less wastefully used.

In addition, the correction or the zero level offsetting is also applicable to other analysis items using the same sample. The reason is that the same sample can also be fed back to other analysis items by single measurement of the reference value.

According to the configuration as described in the present embodiment, it is possible to provide the automatic analysis device in which the biochemical analysis unit and the blood coagulation analysis unit are integrated with each other and which has an excellent throughput, while the reduced device cost or the reduced life-cycle cost is achieved.

According to the present invention, in a case where there is a measurement request for the first test item and the second test item in the same specimen rack, the control unit determines the conveyance path of the specimen rack so that the biochemical analysis unit measures the first test item and the clotting-time analysis unit measures the second test item, and controls the conveyance line. In this manner, it is possible to provide the automatic analysis device which has the excellent throughput.

In addition, in a case where there is a measurement request for the first test item and the second test item in the same specimen rack, the control unit determines the conveyance path of the specimen rack so that the biochemical analysis unit aspirates the specimen and thereafter the clotting-time analysis unit aspirates the specimen, and controls the conveyance line. In this manner, it is possible to provide the automatic analysis device which has the excellent throughput. However, with regard to the arrangement of the analysis unit, the clotting-time analysis unit is not necessarily arranged on the downstream side of the biochemical analysis unit. A configuration can also be adopted in which the clotting-time analysis unit is arranged on the upstream side of the biochemical analysis unit.

In addition, in a case where there is a measurement request for the first test item and the second test item in the same specimen rack, the control unit causes the biochemical analysis unit to aspirate the specimen. Thereafter, in a case where the second dispensing line is vacant, the control unit conveys the specimen rack to the dispensing line (clotting). In a case where the dispensing line (clotting) is not vacant, the control unit controls the conveyance line so as to convey the specimen rack to the rack standby unit. After the dispensing line (clotting) is vacant, the control unit conveys the specimen rack from the rack standby unit to the dispensing line (clotting). In this manner, it is possible to provide the automatic analysis device which has the excellent throughput.

In addition, multiple sample containers are mounted on the specimen rack, and the control unit controls a position of the specimen rack in the dispensing line (clotting) so as to dispense the sample from the sample container in the sequence in which the sample container of the multiple sample containers is determined to need the retest for the second test item. In this manner, it is possible to provide the automatic analysis device which has the excellent throughput.

In addition, in a case where there is a measurement request for all of the first, second, and third test items in the same rack, the control unit controls the conveyance line so as to convey the specimen rack to the second dispensing line in a case where a completion time of aspirating the specimen for the retest of the second test item of the specimen rack is earlier than a time required until it is determined whether or not all of the first and third test items need the retest, when it is determined whether or not all test items of the second test item in the same specimen rack need the retest. In this manner, it is possible to provide the automatic analysis device which has the excellent throughput.

In addition, in addition to a configuration in which the above-described multiple sample containers are mounted on the specimen rack, a configuration can also be adopted in which only a single sample container is mounted on the specimen rack.

REFERENCE SIGNS LIST

101 SPECIMEN RACK
102 RACK SUPPLY UNIT
103 RACK ACCOMMODATION UNIT
104 CONVEYANCE LINE
105 RETURN LINE
106 RACK STANDBY UNIT
107 STANDBY UNIT HANDLING MECHANISM
108 RACK RETURNING MECHANISM
109 RACK DISTRIBUTING MECHANISM
110 RACK LOADING UNIT FOR URGENT SPECIMEN
111 READING UNIT (CONVEYANCE LINE)
112 BIOCHEMICAL ANALYSIS UNIT
113 DISPENSING LINE (BIOCHEMISTRY)
114 RACK CONVEYING MECHANISM (BIOCHEMISTRY)
115 RACK HANDLING MECHANISM (BIOCHEMISTRY)
116 READING UNIT (BIOCHEMISTRY)
117 CLOTTING-TIME ANALYSIS UNIT
118 DISPENSING LINE (CLOTTING)
119 RACK CONVEYING MECHANISM (CLOTTING)
120 RACK HANDLING MECHANISM (CLOTTING)
121 READING UNIT (CLOTTING)
122 CONTROL UNIT
123 STORAGE UNIT
124 DISPLAY UNIT
125 INPUT UNIT
126 AMPLIFIER

The invention claimed is:

1. An automatic analysis device comprising:
a conveyance line configured to convey a specimen rack accommodating one or more specimen containers which respectively hold one or more specimens;
a first dispensing line disposed along the conveyance line, and configured to convey the specimen rack and to cause the specimen rack to stand by thereon;
a biochemical analysis device configured to aspirate one of the specimens from one of the specimen containers accommodated on the specimen rack on the first dispensing line, and to analyze a first test item, which is a synthetic substrate item or a latex agglutination item, in which a first reaction time of a first reagent and the aspirated specimen is predetermined;
a second dispensing line disposed along the conveyance line, and configured to convey the specimen rack and cause the specimen rack to stand by thereon;
a clotting-time analysis device configured to aspirate one of the specimens from one of the specimen containers accommodated on the specimen rack on the second dispensing line, to analyze a second test item, which is a clotting-time measurement item, in which a second reaction time of a second reagent and the aspirated specimen varies depending on the aspirated specimen;
a bar code reader configured to read analysis request information for one of the one or more specimens from at least one of the specimen rack and the one or more specimen containers accommodated on the specimen rack; and
a controller configured to determine a conveyance path of the specimen rack based on the analysis request information from the bar code reader, and that controls the conveyance line, the first dispensing line, and the second dispensing line according to the determined conveyance path,
wherein the controller is further configured to:
determine the conveyance path of a specimen rack accommodating one or more sample containers having specimens in which the read analysis request information indicates a measurement request for the first test item and the second test item in the same specimen rack and control the conveyance line, the first dispensing line, and the second dispensing line so that the biochemical analysis device aspirates all of the specimens having a measurement request for the first test item of the one or more sample containers accommodated on the specimen rack on the first dispensing line, so that the specimen rack is conveyed from the first dispensing line to the second dispensing line and so that the clotting-time analysis device aspirates all of the specimens having a measurement request for the second test item of the one or more sample containers accommodated on the specimen rack on the second dispensing line, and
wherein the biochemical analysis device measures the first test item for the respectively aspirated ones of the specimens having a measurement request for the first test item and the clotting-time analysis device measures the second test item for the respectively aspirated ones of the specimens having a measurement request for the second test item.

2. The automatic analysis device according to claim 1, further comprising:
a rack standby area that is connected to the conveyance line, wherein the controller is further configured to:
when the analysis request information indicates there is the measurement request for the first test item and the second test item in the same specimen rack and when the second dispensing line is vacant after the biochemical analysis device aspirates all of the specimens having a measurement request for the first test item of the one or more specimens from the one or more sample containers accommodated on the specimen rack on the first dispensing line, convey the specimen rack on the conveyance path from the first dispensing line to the conveyance line and further to the second dispensing line, and
when the analysis request information indicates there is the measurement request for the first test item and the second test item in the same specimen rack and when the second dispensing line is not vacant after the biochemical analysis device aspirates all of the specimens having a measurement request for the first test item of the one or more specimens from the one or more sample containers accommodated on the specimen rack on the first dispensing line, convey the specimen rack from the first dispensing line to the conveyance line and further to the rack standby area, and thereafter convey the specimen rack from the rack standby area to the conveyance line and further to the second dispensing line after the second dispensing line is vacant.

3. The automatic analysis device according to claim 1, further comprising:
a rack standby area that is connected to the conveyance line, wherein the controller is further configured to:

after the biochemical analysis device aspirates all of the specimens having a measurement request for the first test item one or more sample containers accommodated on the specimen rack on the first dispensing line and the clotting-time analysis device aspirates all of the specimens having a measurement request for the second test item of the one or more specimens from the one or more sample containers accommodated on the specimen rack on the second dispensing line, convey the specimen rack from the second dispensing line to the conveyance line and further to the rack standby area, and convey the specimen rack from the rack standby area to the conveyance line and further to the second dispensing line in a first retest mode and perform a retest of the second test item, determined to be required for a first time for a plurality of the specimens from the one or more sample containers accommodated on the specimen rack, so that the clotting-time analysis device aspirates all of the specimens from the one or more sample containers accommodated on the specimen rack having a retest measurement request for the second test item.

4. The automatic analysis device according to claim 3, wherein, in the first retest mode, the controller is further configured to:

convey the specimen rack on the second dispensing line so that the plurality of the specimens having a retest measurement request for the second test item are dispensed from the respective sample containers in a sequence based on the order of determination of the requirement for the retest of the second test item of the specimens.

5. The automatic analysis device according to claim 3, wherein the biochemical analysis device is further configured to analyze a third test item, which is a biochemistry measurement item, wherein the controller is further configured to:

when the analysis request information indicates there is the measurement request for the first, second, and third test items in the same specimen rack, and in a second retest mode, convey the specimen rack from the rack standby area to the conveyance line and further to the second dispensing line so that the clotting-time analysis device aspirates all of the specimens having a retest measurement request for the second test item before determining whether or not retest of the first and third test items is required.

6. The automatic analysis device according to claim 5, wherein the controller is further configured to receive a manual selection of the first retest mode and the second retest mode.

7. The automatic analysis device according to claim 5, wherein the controller is further configured to automatically switch between the first retest mode and the second retest mode depending on a status of one of the first test item, the second test item and the third test item.

8. The automatic analysis device according to claim 7, wherein the first retest mode and the second retest mode are automatically switched based on a predetermined number of consecutive requests for the retest of the second test item for the specimens.

9. The automatic analysis device according to claim 1, further comprising:

a storage device connected to the controller, wherein the biochemical analysis device and the clotting-time analysis device pre-measure a reference substance for calculating a reference value relating to an amount of a measurement interference substance contained in a sample, wherein the controller is further configured to obtain a correlation curve between a first reference substance measurement result of the reference substance in the biochemical analysis device and a second reference substance measurement result of the reference substance in the clotting-time analysis device and store the correlation curve in the storage device, wherein the biochemical analysis device is further configured to calculate the reference value relating to the amount of the measurement interference substance contained in the sample prior to the measurement in the clotting-time analysis device, and the clotting-time analysis device corrects the measurement result based on the reference value and the correlation curve.

10. The automatic analysis device according to claim 9, wherein the blood clotting-time analysis device includes a clotting-time detector to detect transmitted light or scattered light and an amplifier which amplifies a signal transmitted from the clotting-time detector, wherein the controller is further configured to control the amplifier to offset a zero level of the amplifier before the clotting-time detector detects the transmitted light or scattered light.

11. The automatic analysis device according to claim 10, wherein, based on a difference between the measurement result in the biochemical analysis device and a preset reference level, the controller is further configured to offset the zero level of the amplifier before the clotting-time detector detects the transmitted light or scattered light.

12. The automatic analysis device according to claim 1, wherein the first reaction time of the first test item is longer than the second reaction time of the second test item.

13. The automatic analysis device according to claim 12, wherein the biochemical analysis device is not configured to analyze the second test item.

* * * * *